United States Patent
Dempsey et al.

(10) Patent No.: US 11,628,314 B2
(45) Date of Patent: Apr. 18, 2023

(54) PLANNING AND CONTROL FOR MAGNETIC RESONANCE GUIDED RADIATION THERAPY

(71) Applicant: ViewRay Technologies, Inc., Oakwood Village, OH (US)

(72) Inventors: James F. Dempsey, Atherton, CA (US); Iwan Kawrykow, Sofia (BG)

(73) Assignee: VIEWRAY TECHNOLOGIES, INC., Oakwood Village, OH (US)

(*) Notice: Subject to any disclaimer, the term of this patent is extended or adjusted under 35 U.S.C. 154(b) by 231 days.

(21) Appl. No.: 17/143,885

(22) Filed: Jan. 7, 2021

(65) Prior Publication Data

US 2021/0146160 A1 May 20, 2021

Related U.S. Application Data

(63) Continuation of application No. 16/166,572, filed on Oct. 22, 2018, now Pat. No. 10,888,714, which is a
(Continued)

(51) Int. Cl.
*A61N 5/10* (2006.01)
*G01R 33/48* (2006.01)

(52) U.S. Cl.
CPC .......... *A61N 5/1064* (2013.01); *A61N 5/107* (2013.01); *A61N 5/1037* (2013.01);
(Continued)

(58) Field of Classification Search
CPC ...... A61N 5/10–1084; A61N 2005/1085–1098
See application file for complete search history.

(56) References Cited

U.S. PATENT DOCUMENTS

| 4,987,309 A | 1/1991 | Klasen |
| 7,640,607 B2 | 1/2010 | Guertin |

(Continued)

FOREIGN PATENT DOCUMENTS

| CN | 101176113 A | 5/2008 |
| CN | 103889506 A | 6/2009 |

(Continued)

OTHER PUBLICATIONS

Lagendijk JJ W et al.: "MRI Guided Radiotherapy: A MRI based linear Accelerator", Radiotherapy and Oncology, vol. 56, No. 01, Sep. 21, 2000 (Sep. 21, 2000), pp. S60-S61.
(Continued)

*Primary Examiner* — Thaddeus B Cox
(74) *Attorney, Agent, or Firm* — Pillsbury Winthrop Shaw Pittman LLP

(57) ABSTRACT

Magnetic resonance (MR) guided radiation therapy (MR-gRT) enables control over the delivery of radiation based on patient motion indicated by MR imaging (MRI) images captured during radiation delivery. A method for MRgRT includes: simultaneously using one or more radiation therapy heads to deliver radiation and an MRI system to perform MRI; using a processor to determine whether one or more gates are triggered based on at least a portion of MRI images captured during the delivery of radiation; and in response to determining that one or more gates are triggered based on at least a portion of the MRI images captured during the delivery of radiation, suspending the delivery of radiation.

12 Claims, 9 Drawing Sheets

Related U.S. Application Data continuation of application No. 15/042,046, filed on Feb. 11, 2016, now abandoned.

(60) Provisional application No. 62/115,105, filed on Feb. 11, 2015.

(52) U.S. Cl.
CPC ......... *A61N 5/1039* (2013.01); *A61N 5/1049* (2013.01); *A61N 5/1071* (2013.01); *A61N 2005/1055* (2013.01); *A61N 2005/1072* (2013.01); *G01R 33/4808* (2013.01)

(56) References Cited

U.S. PATENT DOCUMENTS

| | | | |
|---|---|---|---|
| 7,907,987 | B2 | 3/2011 | Dempsey |
| 7,983,380 | B2 | 7/2011 | Guertin |
| 8,536,547 | B2 | 9/2013 | Maurer, Jr. |
| 8,639,006 | B2 | 1/2014 | Dempsey |
| 8,989,845 | B2 | 3/2015 | Brinks |
| 9,211,423 | B2 | 12/2015 | Gross |
| 9,687,200 | B2 | 6/2017 | Maurer, Jr. |
| 9,764,162 | B1 | 9/2017 | Willcut |
| 9,966,160 | B2 | 5/2018 | Kawrykow |
| 10,124,190 | B2 | 11/2018 | Ojha |
| 2007/0003010 | A1 | 1/2007 | Guertin |
| 2007/0014391 | A1 | 1/2007 | Mostafavi |
| 2008/0312526 | A1 | 12/2008 | Gagnon |
| 2009/0161826 | A1 | 6/2009 | Gertner |
| 2009/0209844 | A1 | 8/2009 | Gagnon |
| 2010/0040197 | A1 | 2/2010 | Maniawski |
| 2010/0113911 | A1 | 5/2010 | Dempsey |
| 2010/0322497 | A1 | 12/2010 | Dempsey |
| 2011/0135190 | A1* | 6/2011 | Maad .................. A61B 6/0407 382/154 |
| 2011/0241684 | A1 | 10/2011 | Dempsey |
| 2011/0288407 | A1 | 11/2011 | Brinks |
| 2011/0301449 | A1 | 12/2011 | Maurer, Jr. |
| 2011/0313231 | A1 | 12/2011 | Guertin |
| 2012/0022363 | A1 | 1/2012 | Dempsey |
| 2012/0189102 | A1 | 7/2012 | Maurer, Jr. |
| 2012/0292534 | A1 | 11/2012 | Geneser |
| 2013/0147476 | A1 | 6/2013 | Shvartsman |
| 2013/0245425 | A1 | 9/2013 | Dempsey |
| 2013/0251099 | A1* | 9/2013 | Kunz .................. A61B 5/0036 378/65 |
| 2013/0267830 | A1 | 10/2013 | Ojha |
| 2013/0296687 | A1 | 11/2013 | Dempsey |
| 2014/0121495 | A1 | 5/2014 | Dempsey |
| 2014/0263990 | A1 | 9/2014 | Kawrykow |
| 2014/0266206 | A1 | 9/2014 | Dempsey |
| 2014/0266208 | A1 | 9/2014 | Dempsey |
| 2014/0275963 | A1 | 9/2014 | Shvartsman |
| 2014/0330108 | A1 | 11/2014 | Dempsey |
| 2014/0347053 | A1 | 11/2014 | Dempsey |
| 2014/0378738 | A1 | 12/2014 | Vajko |
| 2015/0035942 | A1* | 2/2015 | Hampton ............. A61N 5/1049 348/42 |
| 2015/0065860 | A1 | 3/2015 | Shvartsman |
| 2015/0077118 | A1 | 3/2015 | Shvartsman |
| 2015/0154756 | A1 | 6/2015 | Gerganov |
| 2015/0165233 | A1 | 6/2015 | Dempsey |
| 2015/0185300 | A1 | 7/2015 | Shvartsman |
| 2015/0209600 | A1* | 7/2015 | Overweg ............. A61N 5/1049 600/1 |
| 2015/0306423 | A1 | 10/2015 | Bharat |
| 2016/0082288 | A1 | 3/2016 | Vahala |
| 2016/0146911 | A1 | 5/2016 | Chmielewski |
| 2016/0184609 | A1 | 6/2016 | Dempsey |
| 2016/0213947 | A1 | 7/2016 | Han |
| 2016/0228728 | A1 | 8/2016 | Dempsey |
| 2017/0148536 | A1 | 5/2017 | Kawrykow |
| 2017/0273643 | A1 | 9/2017 | Maurer, Jr. |
| 2018/0161602 | A1 | 6/2018 | Kawrykow |
| 2018/0261351 | A1 | 9/2018 | Kawrykow |

FOREIGN PATENT DOCUMENTS

| | | | |
|---|---|---|---|
| CN | 101945685 A | | 1/2011 |
| CN | 102576060 A | | 7/2012 |
| DE | 102005027219 A1 * | 9/2006 | ........... A61N 5/1048 |
| JP | 2002336365 | | 11/2002 |
| JP | 2013506519 | | 2/2013 |
| WO | 20030008986 | | 1/2003 |
| WO | 2005081842 A2 | | 9/2005 |
| WO | 2013171631 | | 11/2013 |
| WO | 2014015421 A1 | | 1/2014 |
| WO | 2014096993 | | 6/2014 |
| WO | 2014170483 | | 10/2014 |

OTHER PUBLICATIONS

Tamada and Kose. 'Two-Dimensional Compressed Sensing Using the Cross-sampling Approach for Low-Field MRI Systems.' IEEE Transactions on Medical Imaging. vol. 33, No. 9. Sep. 2014. pp. 1905-1912.

CN OA dated Mar. 28, 2022, CN Appl. No. 202011072387.3

* cited by examiner

PLANNING AND CONTROL FOR MAGNETIC RESONANCE GUIDED RADIATION THERAPY

RELATED APPLICATIONS

This application is a continuation of and claims priority under 35 U.S.C. § 120 to U.S. patent application Ser. No. 16/166,572, entitled PLANNING AND CONTROL FOR MAGNETIC RESONANCE GUIDED RADIATION THERAPY and filed on Oct. 22, 2018, issued as U.S. Pat. No. 10,888,714, on Jan. 12, 2021, which is a continuation of and claims priority to U.S. patent application Ser. No. 15/042,046, entitled PLANNING AND CONTROL FOR MAGNETIC RESONANCE GUIDED RADIATION THERAPY and filed on Feb. 11, 2016, which claims priority under 35 U.S.C. § 119(e) to U.S. Provisional Patent Application No. 62/115,105, entitled PLANNING AND CONTROL FOR MAGNETIC RESONANCE GUIDED RADIATION THERAPY and filed on Feb. 11, 2015, the disclosures of each are incorporated herein by reference in its entirety.

TECHNICAL FIELD

The subject matter described herein relates to radiation therapy and more particularly to magnetic resonance guided radiation therapy (MRgRT).

RELATED ART

Radiation therapy is frequently used to control and eliminate malignant cells in a patient. For example, a cancerous tumor can be exposed to radiation (e.g., X-rays, gamma rays, and charged particles) during one or more treatment sessions. The effectiveness of radiation therapy depends upon delivering an adequate dose of radiation to a region of interest (ROI), which can include the cancerous tumor as well as areas of potential disease spread. At the same time, the radiation should be delivered in a manner that spares organs at risk (OARs).

Conventionally, radiation therapy treatments are planned and administered based on the contours and positions of ROIs and OARs as defined in static medical imaging scans (e.g., computed tomography (CT), magnetic resonance imaging (MRI)). Thus, conventional radiation therapy does not account for patient motion during treatment. For example, patient organ geometry may shift significantly during treatment due to voluntary and/or involuntary movements (e.g., respiration, muscle contractions). Consequently, the actual dose of radiation delivered to the ROI and the extent to which OARs are subject to radiation are likely to deviate from the intended treatment plan. As such, conventional radiation therapy can be less effective than desirable.

SUMMARY

Systems and methods for MRgRT are provided. Implementations of the current subject matter improve the administration of radiation therapy including by simultaneously delivering radiation and performing MRI. The delivery of radiation can be controlled based on patient motion indicated by MRI images captured during the delivery or radiation. One or more mechanisms can be deployed during the delivery of radiation to terminate radiation delivery based on patient motion.

Implementations of the current subject matter include a method for MRgRT. The method can include: simultaneously using one or more radiation therapy heads to deliver radiation and an MRI system to perform MRI; using a processor to determine whether one or more gates are triggered based on at least a portion of MRI images captured during the delivery of radiation; and in response to determining that one or more gates are triggered based on at least a portion of the MRI images captured during the delivery of radiation, suspending the delivery of radiation.

Implementations of the current subject matter include a system for MRgRT. The system can include an MRgRT apparatus and a processor coupled to the MRgRT apparatus.

The MRgRT apparatus can include one or more radiation therapy heads and an MRI system. The MRgRT apparatus can be configured to simultaneously use the one or more radiation therapy heads to deliver radiation and the MRI system to perform MRI.

The processor can be configured to: determine whether one or more gates are triggered based on at least a portion of MRI images captured during the delivery of radiation; and in response to determining that one or more gates are triggered based on at least a portion of the MRI images captured during the delivery of radiation, suspend the delivery of radiation.

Implementations of the current subject matter include a method for MRgRT. The method can include: receiving a plurality of MRI images captured by an MRI system during a delivery of radiation by one or more radiation therapy heads; determining, based on a least a portion of the MRI images, whether one or more gates are triggered; and in response to determining that the one or more gates are triggered based on at least a portion of the MRI images, causing the one or more radiation therapy heads to suspend delivery of radiation.

Implementations of the current subject matter can include, but are not limited to, methods consistent with the descriptions provided herein as well as articles that comprise a tangibly embodied machine-readable medium operable to cause one or more machines (e.g., computers, etc.) to result in operations implementing one or more of the described features. Similarly, computer systems are also described that may include one or more processors and one or more memories coupled to the one or more processors. A memory, which can include a non-transitory computer-readable or machine-readable storage medium, may include, encode, store, or the like one or more programs that cause one or more processors to perform one or more of the operations described herein. Computer implemented methods consistent with one or more implementations of the current subject matter can be implemented by one or more data processors residing in a single computing system or multiple computing systems. Such multiple computing systems can be connected and can exchange data and/or commands or other instructions or the like via one or more connections, including but not limited to a connection over a network (e.g. the Internet, a wireless wide area network, a local area network, a wide area network, a wired network, or the like), via a direct connection between one or more of the multiple computing systems, etc.

The details of one or more variations of the subject matter described herein are set forth in the accompanying drawings and the description below. Other features and advantages of the subject matter described herein will be apparent from the description and drawings, and from the claims. While certain features of the currently disclosed subject matter are described for illustrative purposes in relation to radiation therapy, it should be readily understood that such features are not intended to be limiting. The claims that follow this disclosure are intended to define the scope of the protected subject matter.

BRIEF DESCRIPTION OF THE DRAWINGS

The accompanying drawings, which are incorporated in and constitute a part of this specification, show certain aspects of the subject matter disclosed herein and, together with the description, help explain some of the principles associated with the disclosed implementations. In the drawings.

DETAILED DESCRIPTION

Conventional approaches for administering radiation therapy generally do not account for patient motion during radiation delivery. The isocenter placement and beam configuration are generally performed during treatment planning on the basis of static images (e.g., MRI, CT). However, shifts in patient organ geometry are likely to occur during treatment. For example, respiration and muscle contractions can deform the contours of anatomical structures (e.g., ROIs, OARs) as well as change their positions. As a result, an ROI can move outside of the paths of radiation beams as set forth in the original treatment plan thereby reducing the actual dose of radiation delivered to the area. Similarly, an OAR may move into the paths of radiation beams and be subjected to an unintended amount radiation.

Various implementations of the current subject matter can include systems and methods for MRgRT that provide dynamic controls for the delivery of radiation. Implementations of the current subject matter can include a gating mechanism which imposes one or more spatial and/or temporal gates for controlling the delivery of radiation. Some implementations of the current subject matter can further include an interlock mechanism, which detects gross patient movement and suspends radiation delivery accordingly. Gating and interlock mechanisms consistent with the present disclosure can operate based on MRI images (e.g., planar, volumetric) including MRI images captured during the delivery of radiation.

Figure 1:
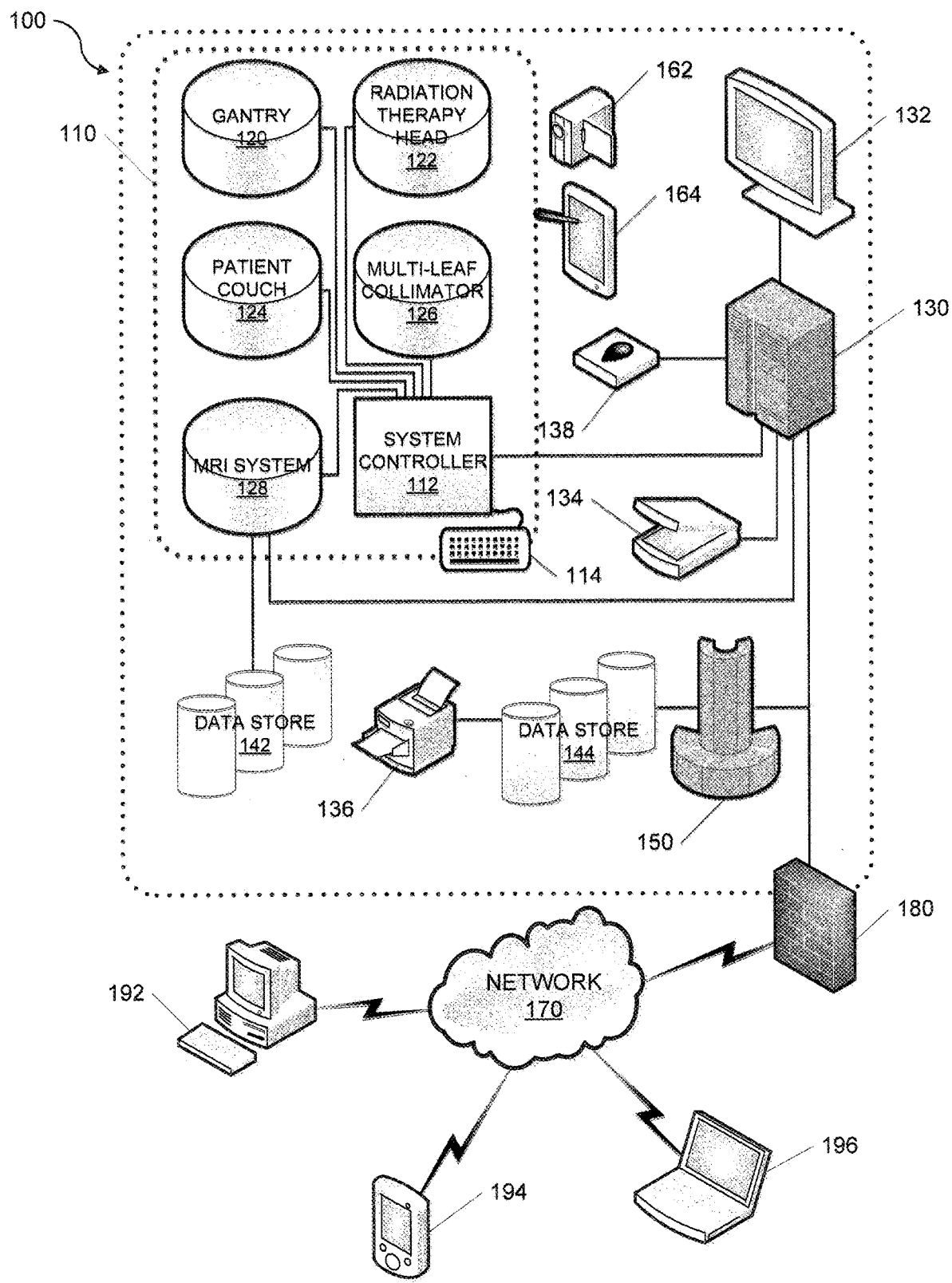
FIG. 1 is a network diagram illustrating an MRgRT system consistent with implementations of the current subject matter.

FIG. 1 is a system diagram illustrating an MRgRT system 100 consistent implementations of the current subject matter. Referring the FIG. 1, the MRgRT system 100 can include a system controller 112, a gantry 120, a radiation therapy head 122, a patient couch 124, a multi-leaf collimator 126, and an MRI system 128.

The system controller 112 is configured to control the operations of the gantry 120, the radiation therapy head 122, the patient couch 124, the multi-leaf collimator 126, and the MRI system 128. The system controller 112 can be coupled to a control console 114. Via the control console 114, a user may control the operations of the system controller 112 thereby controlling the operations of one or more of the gantry 120, the radiation therapy head 122, the patient couch 124, the multi-leaf collimator 126, and the MRI system 128.

During a radiation therapy session, the radiation therapy head 122 may deliver one or more beams of radiation. The system controller 112 may rotate the gantry 120 and/or the patient couch 124 such that a patient on the patient couch 124 is properly positioned to receive the radiation beams (e.g., at an ROI) from the radiation therapy head 122.

The radiation therapy head 122 can be implemented by any device that can be a source of radiation or a linear particle accelerator (LINAC) without departing from the scope of the present disclosure. For example, the radiation therapy head 122 can be a radioisotope source using isotopes including, for example, but not limited to, cobalt (e.g., cobalt-60 ($^{60}$Co)) and iridium (e.g., iridium-192 ($^{192}$Ir)). Alternately or in addition, the radiation therapy head 122 can also provide particle therapy as an LINAC. Furthermore, although the MRgRT system 100 is shown to include a single radiation therapy head, the MRgRT system 100 can include additional radiation therapy heads without departing from the scope of the present disclosure.

In some implementations of the current subject matter, the MRgRT system 100 may administer intensity modulated radiation therapy (IMRT) or conformal radiation therapy (CRT). As such, the system controller 112 may engage the multi-leaf collimator 126. The multi-leaf collimator 126 includes a plurality of "leaves" of heavy metal material (e.g., lead (Pb), tungsten (W)) that alter the shape of the radiation beam from the radiation therapy head 122 by blocking at least some portions of the radiation beam. The shape of the radiation beam can be adjusted (e.g., via the system controller 112) by changing the configuration of the leaves in the multi-leaf collimator 126. It is to be understood that references to radiation therapy throughout the present disclosure contemplates a variety of different types and forms of radiation therapy including, for example, but not limited to, IMRT and CRT.

In some examples, the system controller 112, the control console 114, the gantry 120, the radiation therapy head 122, the patient couch, the multi-leaf collimator 126, and the MRI system 128 can be part of an MRgRT apparatus 110 capable of simultaneously delivering radiation and performing MRI. The MRgRT apparatus 110 is described in further detail in co-owned U.S. Pat. No. 7,907,987, the disclosure of which is incorporated herein by reference in its entirety.

The MRI system 128 captures planar (i.e., 2-dimensional (2D)) and/or volumetric (i.e., 3-dimensional (3D)) MRI images. The MRI system 128 can be configured to capture MRI images of the patient during the delivery of radiation.

The MRI system 128 can also capture MRI images as part of motion-based treatment planning and throughout the course of radiation therapy treatment. For example, the MRI system 128 may capture planar and/or volumetric MRI images at a certain rate (e.g., 4 frames per second). Advantageously, a sequential series of planar and/or volumetric MRI images captured by the MRI system 128 during the delivery of radiation enables tracking of patient motions (e.g., shift in patient organ geometry) during the delivery of radiation. The MRI system 128 can store such data (e.g., 4-dimensional (4D) MRI image data) in a first data store 142.

The MRgRT system 100 includes a user interface system 130. The user interface system 130 can provide one or more input/output (I/O) mechanisms including, for example, but not limited to, a display 132, a scanner 134, a printer 136, and a security reader 138. A user (e.g., a radiotherapist) can interact with the MRgRT system 100 via the one or more I/O mechanisms. For example, the user can be authenticated to access the MRgRT system 100 via the security reader 138 using one or more mechanisms including, for example, but not limited to, biometrics and radio frequency identification (RFID) tags. The user can also configure the MRgRT system 100 via the user interface system 130 to perform one or more operations associated with the administration of radiation therapy including, for example, but not limited to, treatment planning, execution, and optimization.

The MRgRT system 100 can further include a processor 150, which can monitor for when gates are triggered and/or when interlock thresholds are exceeded based on MRI images (e.g., 4D) captured by the MRI system 128 during radiation delivery. The processor 150 can also be configured to generate and/or modify one or more treatment plans. In addition, the processor 150 can calculate the actual dose of radiation that was delivered a patient during a radiation therapy treatment session based on the MRI images captured during the delivery of radiation. The actual dose of radiation that was delivered to the patient can be affected by patient motion (e.g., change in patient organ geometry) during the delivery of radiation as well as interruptions to radiation delivery caused by the gating mechanism and/or the interlocking mechanism.

The MRgRT system 100 can also be configured to track the cumulative dose of radiation delivered to a patient. As such, the processor 150 may accrue the actual dose of radiation delivered to a patient during individual radiation therapy treatment sessions.

In some implementations of the current subject matter, the MRgRT system 100 can provide a patient monitoring and communication system 162. For example, the patient monitoring and communication system 162 can include a camera and/or a microphone. The MRgRT system 100 can further include a patient audio/video (A/V) entertainment system 164. For example, the patient A/V entertainment system 164 can be portable electronic device such as a tablet personal computer (PC).

The MRgRT system 100 supports access by a plurality of remote users including, for example, but not limited to, a first remote user 192, a second remote user 194, and a third remote user 196. Remote users may access the MRgRT system 100 via a wired and/or wireless network 170 to perform tasks including, for example, but not limited to, radiation therapy treatment planning, approvals, and scheduling. Access to the MRgRT system 100 by remote users can be monitored and regulated by a firewall 180. The MRgRT system 100 can include additional and/or different components than shown without departing from the scope of the present disclosure.

Figure 2:
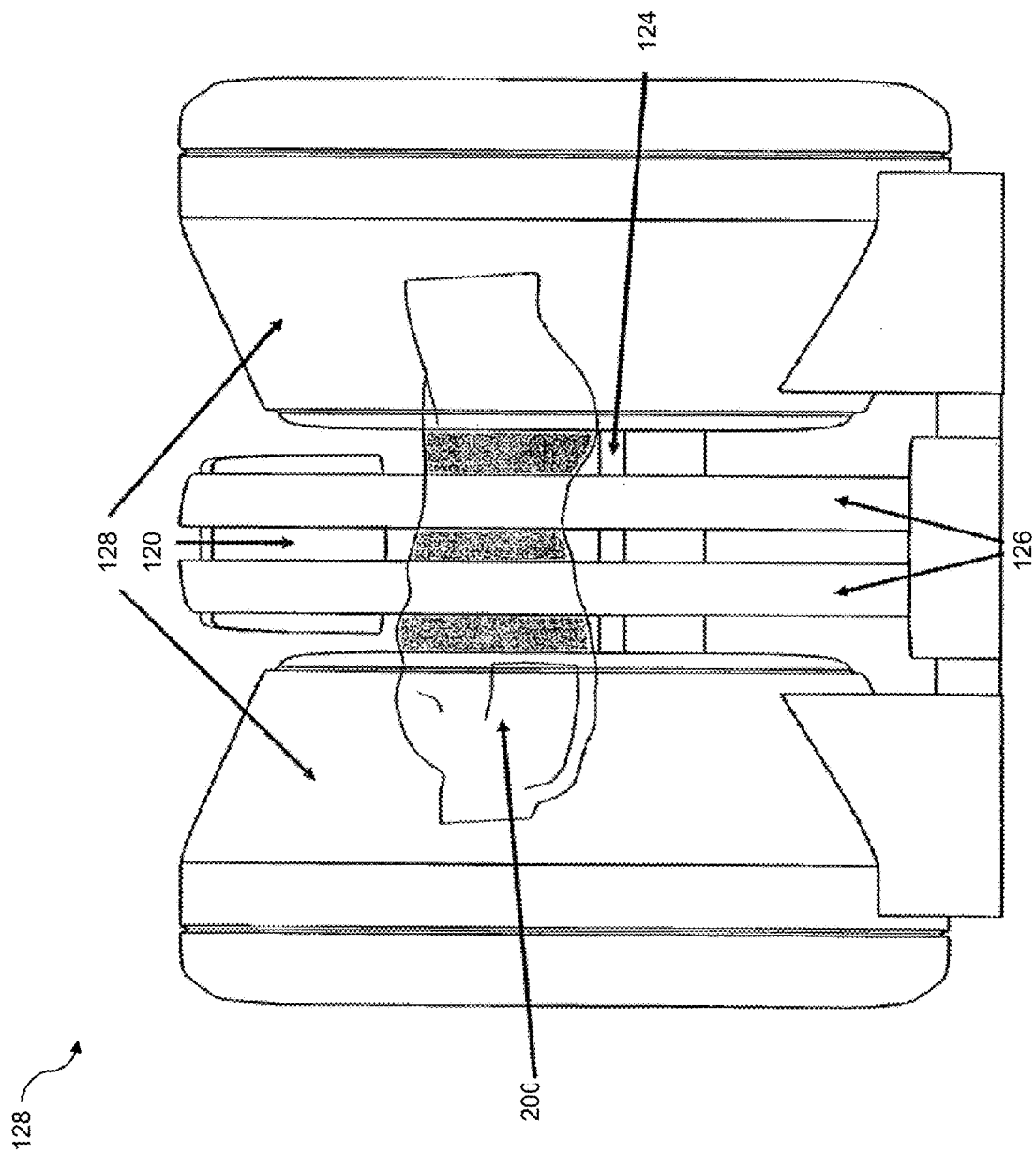
FIG. 2 is a cross-sectional view illustrating an MRgRT apparatus consistent with implementations of the current subject matter.

FIG. 2 is a cross-sectional view illustrating the MRgRT apparatus 110 consistent with implementations of the current subject matter. Referring to FIGS. 1 and 2, the MRgRT apparatus 110 includes the gantry 120, the multi-leaf collimator 126, the patient couch 124, and the MRI system 128. Consistent with implementations of the current subject matter, a patient 200 can be placed on the patient couch 124. The patient 200 can receive radiation from the radiation therapy head 122 while the MRI system 128 simultaneously captures one or more MRI images of the patient 200. The MRgRT apparatus 110 can include additional and/or different components than shown without departing from the scope of the present disclosure.

Figure 3:
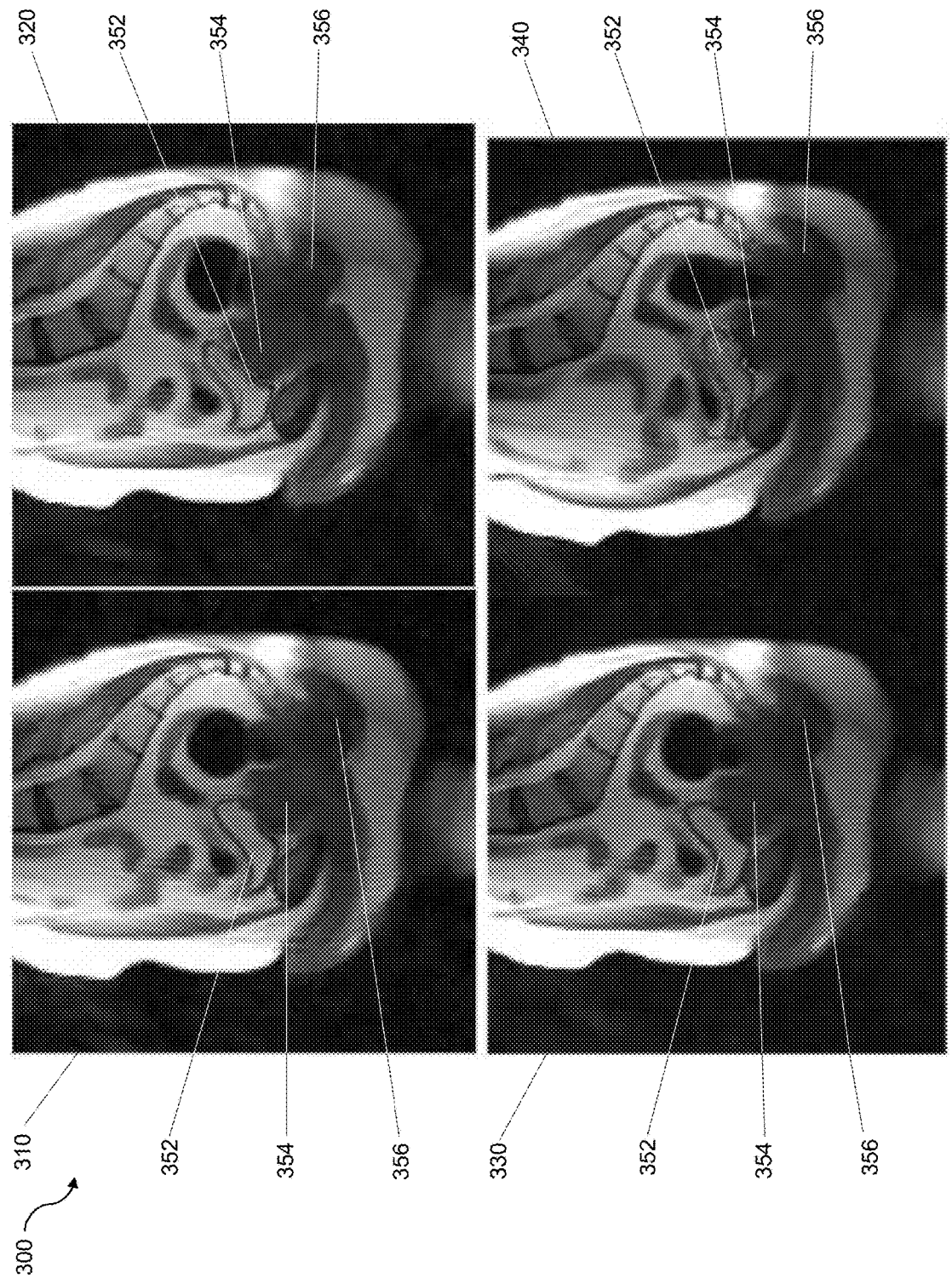
FIG. 3 illustrates a series of MRI images consistent with implementations of the current subject matter.

FIG. 3 illustrates a series 300 of MRI images consistent with implementations of the current subject matter. Referring to FIGS. 1, 2, and 3, the series 300 of MRI images depict patient motion, such as during the delivery of radiation. The MRgRT system 100 (e.g., the MRI system 128) can capture the MRI images of the series 300 as part of motion-based treatment planning, while a patient is undergoing radiation therapy, and/or throughout the course of radiation therapy treatment. As shown, the series 300 includes a first MRI image 310, a second MRI image 320, a third MRI image 330, and a fourth MRI image 340.

A change in the patient's organ geometry resulting from a muscle contraction is depicted in the first MRI image 310 and the second MRI image 320. For example, as shown in the first MRI image 310 and the second MRI image 320, a contraction of the patient's gluteus muscles results in a shift in the position of the bladder 352.

A change in the patient's organ geometry resulting from respiration is depicted in the third MRI image 330 and the fourth MRI image 340. For example, as shown in the third MRI image 330 and the fourth MRI image 340, taking a breath causes a shift in the positions of the bladder 352, the prostate 354, and the rectum 356.

Figure 4A:
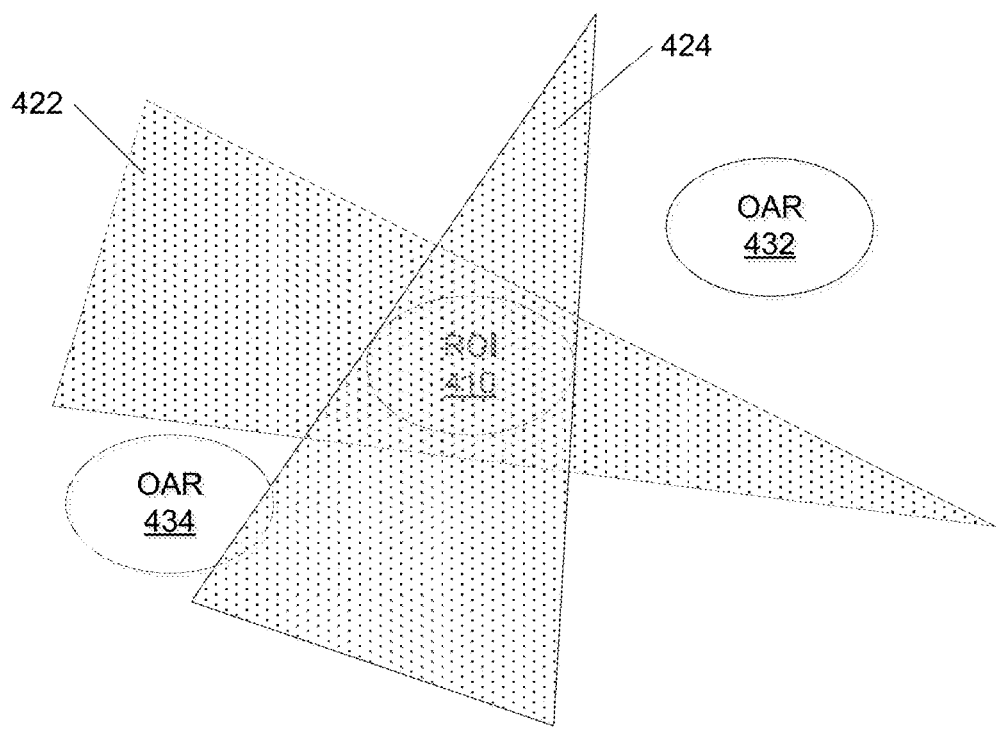
FIG. 4A illustrates the delivery of one or more radiation beams consistent with implementations of the current subject matter.

FIG. 4A illustrates the delivery of one or more radiation beams consistent with implementations of the current subject matter. Referring to FIG. 4A, a patient's radiation therapy treatment can include delivering a plurality of radiation beams to an ROI 410, including, for example, a first radiation beam 422 and a second radiation beam 424. The patient's radiation therapy treatment can be planned by placing the first radiation beam 422 and the second radiation beam 424 such that the ROI 410 is subject to maximum exposure to the first radiation beam 422 and the second radiation beam 424. Moreover, the patient's radiation therapy treatment can be planned by placing the first radiation beam 422 and the second radiation beam 424 such that a first OAR 432 and a second OAR 434 are subject to minimal exposure to the first radiation beam 422 and the second radiation beam 424.

Figure 4B:
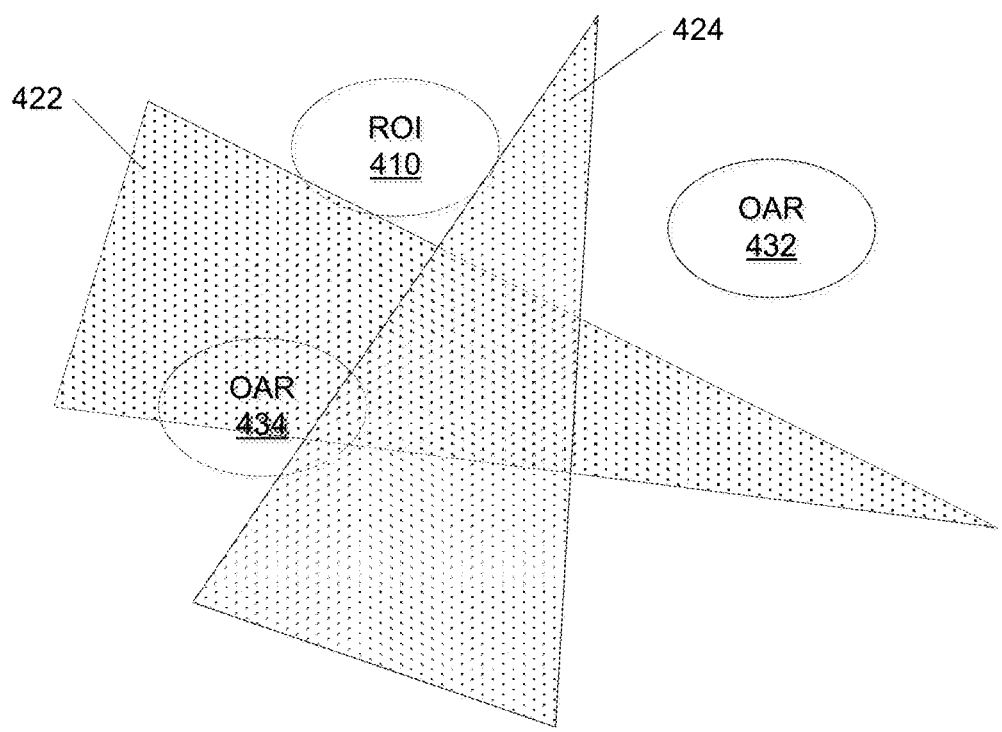
FIG. 4B illustrates the delivery of one or more radiation beams consistent with implementations of the current subject matter.

FIG. 4B illustrates the delivery of one or more radiation beams consistent with implementations of the current subject matter. Referring to FIGS. 4A-B, patient motion during radiation therapy can change patient organ geometry and cause the delivery of radiation beams to deviate from the treatment plan.

For example, as shown in FIG. 4B, patient motion during radiation therapy may cause the ROI 410 to shift outside of the paths of the first radiation beam 422 and the second radiation beam 424 as placed in accordance with the treatment plan. Alternately or in addition, patient motion during radiation therapy may cause the second OAR 434 to shift into the paths of the first radiation beam 422 and the second radiation beam 434 as placed in accordance with the treatment plan. As a result, the actual dose of radiation delivered to the ROI 410 is less than planned while the second OAR 434 is exposed to a higher dose of radiation than planned.

Figure 5:
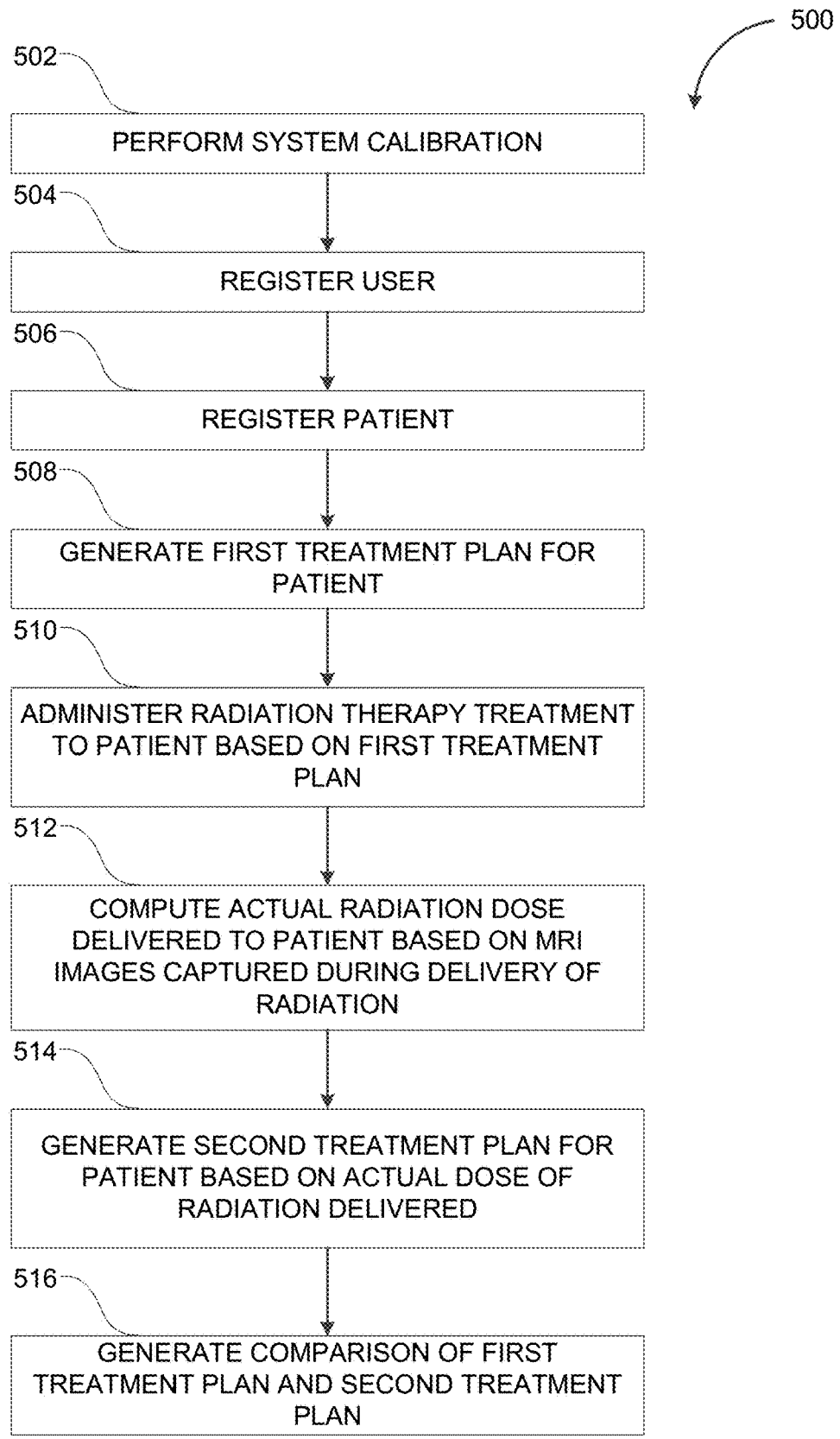
FIG. 5 is a flowchart illustrating an MRgRT process consistent with implementations of the current subject matter.

FIG. 5 is a flowchart illustrating an MRgRT process 500 consistent with implementations of the current subject matter. Referring to FIGS. 1, 2, and 5, the MRgRT process 500 can be performed by the MRgRT system 100 described with respect to FIG. 1.

The MRgRT system 100 performs system calibration (502). For example, a calibrated output of the radiation therapy head 122 and measured radiation therapy calibration data can be input into the MRgRT system 100 when installing, commissioning, reconfiguring, and/or updating the MRgRT system 100. In addition, data for calibrating the MRI system 128 can also be acquired and/or computed. Data for calibrating the MRgRT system 100 including the MRI system 128 can include, for example, but not limited to, dosimetric output of cobalt sources (e.g. if the radiation therapy is performed using a radioisotope source) in a reference geometry as required by calibration protocols, relative dose output for various field sizes, 1-3 dimensional dose distribution data of defined beam geometries, and MRI phantom data. The user interface 130 can be configured to display at least a portion of the calibration data in overlay, percent difference, and absolute difference. Additionally, the MRgRT system 100 can also store the calibration data (e.g., in the first data store 142 and/or the second data store 144) and/or output the calibration data (e.g., via the printer 136). Integrity of the calibration data can be ensured by storing redundant copies of the calibration data and/or applying a cyclically redundant checksum algorithm.

The MRgRT system 100 can register a user (504). A user (e.g., a radiotherapist) can be required to register prior to operating the MRgRT system 100. User registration can include recording one or more forms of identification information including, for example, but not limited to, username, password, photograph, and biometrics. At least some users can be defined as administrative users having the capability to set privileges and tasks for other users with respect to the MRgRT system 100. Access to the MRgRT system 100 can require successful user registration and authentication. However, in some example implementations, a user can bypass user registration and/or authentication by providing one or more forms of identification information including, for example, but not limited to, a photograph and biometrics.

The MRgRT system 100 can register a patient (506). A patient can be required to register in order to undergo medical imaging and/or radiation therapy treatments administered by the MRgRT system 100. Patient registration can include recording one or more forms of identification information including, for example, but not limited to, patient name, password, photograph, and biometrics. In addition, patient registration can include collecting personal data including, for example, but not limited to, age, date of birth, gender, weight, race, address, medical data, treatment instructions, contact information, and A/V entertainment preferences.

Prior to undergoing medical imaging and/or receiving radiation therapy treatments, the MRgRT system 100 can require patient authentication based on identification information including, for example, but not limited to, patient name, date of birth, social security number, photo identification, and biometrics. In some example implementations, in an emergency situation (e.g., an emergent spinal cord compression), patient registration and/or authentication can be bypassed.

The MRgRT system 100 generates a first treatment plan for the patient (508). Consistent with implementations of the current subject matter, treatment planning includes a plurality of operations including, for example, but not limited to, MRI image acquisition, contouring (e.g., of ROIs and/or OARs), prescription, and delivery configuration. In some implementations of the current subject matter, the planned treatment can include IMRT. As such, treatment planning can further include IMRT configurations.

In some example implementations, a gating mechanism can be deployed during radiation delivery. The gating mechanism monitors the positions of anatomical structures (e.g., ROIs and/or OARs) using MRI images captured by the MRgRT system 100 (e.g., the MRI system 128) during the delivery of radiation and suspends radiation delivery based on spatial and/or temporal "gates." For example, the gating mechanism can be configured to suspend radiation delivery in the event that an ROI or an OAR shifts and remains across of one or more spatial gates (e.g., 3 millimeters (mm)) for a length of time in excess of the temporal gate (e.g., 3 seconds). As such, the first treatment plan can include definitions of one or more spatial and/or temporal gates.

One or more spatial gates can be defined based on a baseline set of MRI images depicting the default or resting positions of a patient's anatomical structures (e.g., ROIs and/or OARs). The MRgRT system 100 can provide, via the user interface 130, a graphic user interface (GUI) for a user (e.g., a radiologist) to indicate the position of one or more spatial gates on the baseline set of MRI images.

In some implementations of the current subject matter, one or more spatial gates can be set based on a patient's treatment plan (e.g., the first treatment plan) to indicate a region that is expected to receive a high dose of radiation. Alternately or in addition, the user can set one or more spatial gates based on overlap between the patient's anatomical structures (e.g., ROIs and OARs) as depicted in the MRI images and those regions expecting to receive high radiation doses. The MRgRT system 100 can provide tools to enables the user to visually set one or more spatial gates based on planar or volumetric representations of ROIs (e.g., generated based on the MRI images) and/or regions expecting to receive high doses of radiation. In addition, a spatial gate can be set with fractional gating parameters such that the spatial gate is triggered based on a fractional or percentage overlap in a 2D or 3D region. Advantageously, spatial gates ensure that an ROI is exposed to radiation only when the ROI is within the gated region subject to high radiation dose. Alternately or in addition, the gates can also ensure that an OAR is spared from being exposed to a high radiation dose when the OAR enters the gated region subject to high radiation dose.

In some implantations of the current subject matter, the user can also set and assign temporal gates to one or more spatial gates. The temporal gates impose a numerical time delay such that a spatial gate is triggered by patient motions (e.g., changes in patient organ geometry) that are maintained over a threshold period of time (e.g., 3 seconds).

Alternately or in addition, in some implementations of the current subject matter, an interlock mechanism can be deployed during radiation delivery. The interlock mechanism is configured to suspend radiation delivery in response to detecting significant and/or excessive patient motion (e.g., change in patient organ geometry) in MRI images (e.g., planar) captured by during the delivery of radiation. As such, the first treatment plan can also include one or more thresholds triggering the interlock mechanism.

Consistent with implementations of the current subject matter, the interlock mechanism can operate based on fast numerical evaluations of image characteristics including, for example, but not limited to, image intensity (e.g., of MRI images). For example, the interlock mechanism can operate based on loss of image intensity (e.g. blank images), total change in pixel intensity between consecutive images or image sets, and/or large changes in variance between consecutive images or image sets. Changes in image intensity can indicate that the MRI system 128 is not operating correctly and/or rapid and excessive patient motion. Accordingly, the delivery of radiation can be terminated until the condition is resolved such as when rapid and excessive patient motion has ceased.

The MRgRT system 100 administers radiation therapy treatment to the patient based at least in part on the first treatment plan (510). Consistent with implementations of the current subject matter, treatment administration can include a plurality of operations including, for example, but not limited to, initial and/or continued adjustments of patient position (e.g., on the patient couch 124), MRI, and radiation delivery.

In one implementation of the current subject matter, the MRgRT system 100 simultaneously delivers radiation (e.g., via the radiation therapy head 122) and performs MRI (e.g., using the MRI system 128). Advantageously, MRI images captured during radiation delivery can be used to detect patient motion. The MRgRT system 100 can control the delivery of radiation to a patient based on patient motion detected during radiation delivery.

In some implementations of the current subject matter where a gating mechanism is deployed during radiation delivery, treatment administration can further include operations to recommence radiation delivery that has been suspended by the gating mechanism. Alternately or in addition, when an interlock mechanism is deployed during radiation delivery, treatment administration can also include operations to recommence radiation delivery that has been suspended by the interlock mechanism. For example, the MRgRT system 100 can recommence radiation delivery when one or more conditions causing the suspension of radiation delivery has been resolved (e.g., cessation of patient motion, anatomical structure returns within spatial gates).

In some implementations of the current subject matter, the MRgRT system 100 is configured to store (e.g., in the first data store 142 and/or the second data store 144) at least a portion of the data collected (e.g., MRI images captured by the MRI system 128) during radiation delivery. For example, data collected from a patient's earlier radiation therapy treatment sessions can be used to generate subsequent treatment plans for the patient.

The MRgRT system 100 computes an actual dose of radiation delivered to the patient based on MRI images captured during radiation therapy (512). The actual dose of radiation delivered to the patient can be affected by patient motion (e.g., shift in patient organ geometry) during the delivery of radiation and interruptions to radiation delivery caused by the gating mechanism and/or the interlock mechanism.

The MRgRT system 100 can compute actual dose by performing deformable image registration to identify anatomical structures (e.g., ROIs, OARS) that demonstrated motion exceeding one or more thresholds during radiation delivery. Additionally, in some implementations of the current subject matter, the MRgRT system 100 can compute actual dosage by also identifying anatomical structures that were exposed to radiation. The MRgRT system 100 can generate one or more dose volume histograms (DVH) reflecting the actual dosage delivered to the patient.

The MRgRT system 100 generates a second treatment plan for the patient based on the actual dose of radiation delivered (514). Consistent with implementations of the current subject matter, the MRgRT system 100 can generate a second treatment plan for subsequent radiation therapy treatments based on the actual dose of radiation that was delivered to a patient during one or more previous radiation therapy treatments.

The second treatment plan can include changes to the prescription and/or delivery configuration indicated by the first treatment plan including, for example, but not limited to, increasing radiation dose to an ROI that received insufficient doses of radiation during earlier radiation therapy treatments, decreasing radiation dose to an OAR exposed to an excessive doses of radiation, changing beam placement, and changing IMRT configurations.

In some implementations of the current subject matter, generating the second treatment plan can further include acquiring additional MRI images (e.g., 4D MRI images collected during radiation delivery). The MRgRT system 100 can generate the second treatment plan to include additional adjustments to the prescription indicated by the first treatment plan based on the MRI images. The second treatment plan can further include changes to one or more gates (e.g., spatial, temporal) and/or one or more interlock thresholds defined in the first treatment plan for the interlock mechanism.

The MRgRT system 100 generates a comparison of the first treatment plan and the second treatment plan (516). Consistent with implementations of the current subject matter, the MRgRT system 100 can generate a side-by-side comparison of a plurality of treatment plans. Multiple treatment plans can be compared with respect to plan parameters including, for example, but not limited to, DVHs, hot and cold spots in dose distribution, and radiation beam parameters (e.g., duration, segment quantity, angle, isocenter radiological depth).

The MRgRT system 100 can provide alerts when the discrepancy between two treatment plans exceeds one or more thresholds. For example, the MRgRT system 100 can display (e.g., on the display 132 coupled to the user interface 130) dose distributions orthogonally from an MRI image set of the patient. The MRgRT system 100 can indicate differences in dose distribution between multiple treatment plans including by displaying an overlay of the DVHs associated with various treatment plans.

One or more operations of the process 500 can be performed in a different order than shown without departing from the scope of the present disclosure. Moreover, one or more operations of the process 500 can be repeated and/or omitted without departing from the scope of the present disclosure.

Figure 6:
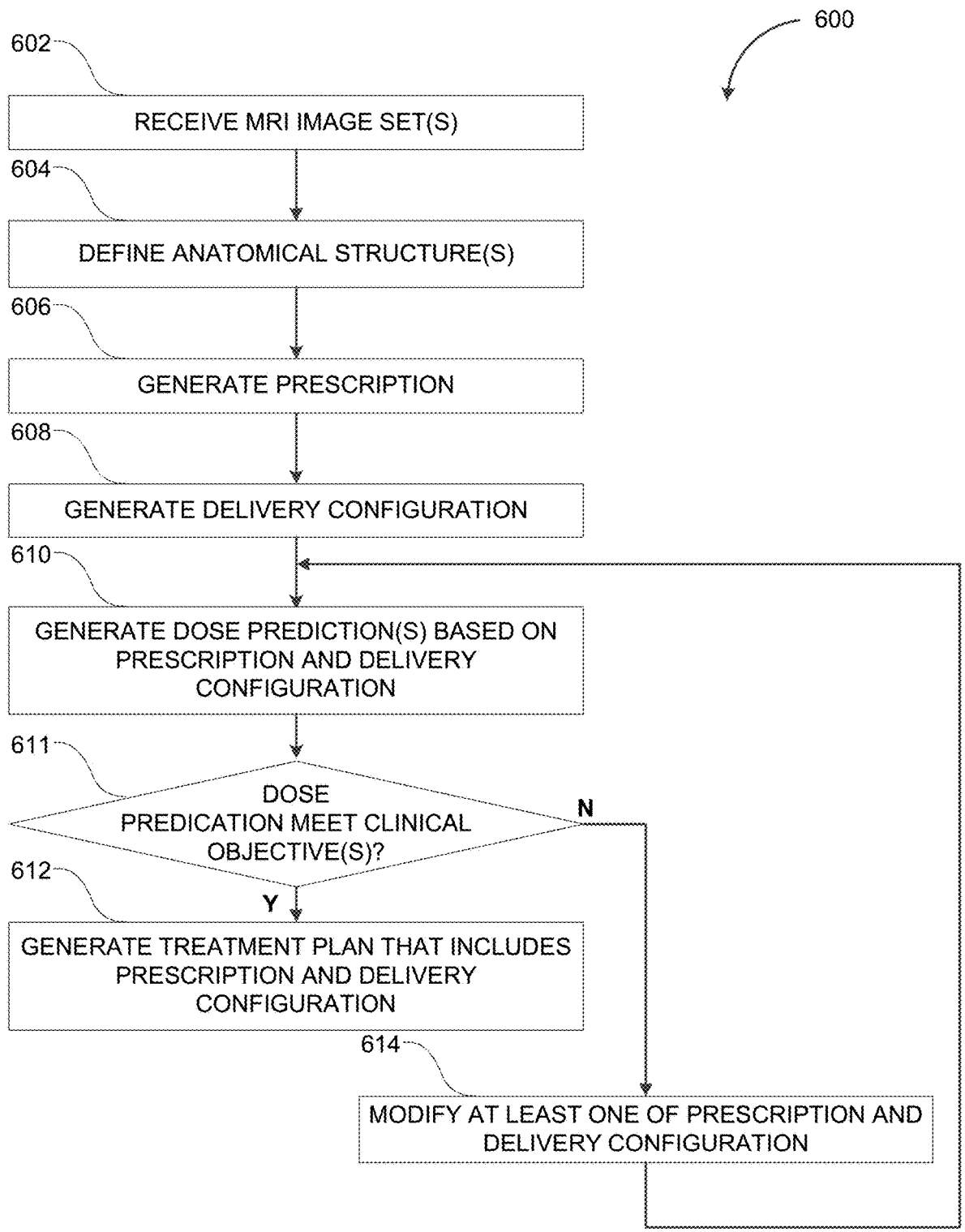
FIG. 6 is a flowchart illustrating a process for treatment planning consistent with implementations of the current subject matter.

FIG. 6 is a flowchart illustrating a process 600 for treatment planning consistent with implementations of the current subject matter. Referring to FIGS. 1, 5, and 6, the process 600 can be performed by the MRgRT system 100 and can implement operation 508 and/or operation 516 of the process 500 described with respect to FIG. 5.

The MRgRT system 100 receives at least one MRI image set (602). The MRgRT system 100 can require at least one MRI image set in order to generate a treatment plan. In some implementations of the current subject matter, the MRgRT system 100 can receive multimodality MRI image sets, which integrates various different types of medical imaging (e.g., MRI, CT, positron emission tomography (PET), ultrasound).

The MRgRT system 100 defines one or more anatomical structure based at least in part on the MRI image set (604). In some implementations of the current subject matter, the MRgRT system 100 can automatically determine the contours of one or more of a patient's ROIs and OARs. For example, the MRgRT system 100 performs auto contouring based on anonymous existing data sets and/or earlier data sets from the patient. The MRgRT system 100 can require automatically generated contours to be manually validated.

Automatic contours can be a deforming contour or a non-deforming contour. A deforming contour adjusts its shape and/or volume to match the anatomical structure (e.g., ROI, OAR) when placed on an MRI image. Conversely, a non-deforming contour retains its shape and volume when superimposed upon an MRI image. A non-deforming contour is adapted tracking a region of malignant cells (e.g., clinical targets) that require the same or higher dosage even when the region is receding or has vanished.

Alternately or in addition, the MRgRT system 100 can also provide, via the user interface 130, one or more mechanisms for manually segmenting and contouring the patient's anatomy including, for example, but not limited to, outlining tools and voxel painting tools. The MRgRT system 100 can provide a library of anatomical structure names, including custom names added by one or more users, for labeling defined ROIs and/or OARs.

In some implementations of the current subject matter, an anatomical structure can be defined as an intra-fraction MRI image target volume (ITV). The MRgRT system 100 can generate an ITV as the union of an anatomical structure depicted throughout an MRI image set. Alternately, the MRgRT system 100 can generate an ITV as the time weighted average of the anatomical structure depicted throughout an MRI image set. Newly created ITVs can be compared to existing ITVs in the orthogonal views on the original MRI image set to create a set of corresponding segmentation contours.

In some implementations of the current subject matter, multiple sets of contours (e.g., automatic and/or manual) can be available and/or created for a single anatomical structure. For example, the MRgRT system 100 can receive multiple sets of MRI images throughout the course of radiation therapy treatment. As such, the MRgRT system 100 can provide at least some of the contours (e.g., via the user interface 130) in a manner that enables a user to compare the different contours. For example, the MRgRT system 100 can provide at least some of the contours in an overlay with axial, sagital, and/or coronal orthogonal views. Alternately or in addition, the different contours can be shown as voxels in a color wash display.

The MRgRT system 100 generates a prescription (606). Consistent with implementations of the current subject matter, the prescription can include radiation doses (e.g., dose-volume, dose to points) to be delivered to a patient's ROIs and margins for expansion. The prescription can further include various tolerances that include, for example, but not limited to, dose-volume constraints for OARs. The various tolerances can set limits used for dose prediction and on-table treatment plan re-optimization during the administration of radiation therapy treatment.

In some implementations of the current subject matter, the prescription can also include one or more spatial and temporal gates to be applied when the gating mechanism is deployed during the administration of radiation therapy treatment. The one or more spatial gates can be determined based on MRI images captured by the MRgRT system 100 (e.g., the MRI system 128) during the delivery of radiation.

The prescription can also include additional treatment parameters including, for example, but not limited to, requirements or prohibitions for planar imaging, volumetric imaging, dose prediction, on-table re-optimization, 4D MRI image data acquisition, MRI image target volume (ITV) target generation, planar gating, and delivered dose evaluation.

Consistent with implementations of the current subject matter, the radiation doses and tolerances specified in the prescription can be determined based on the cumulative actual radiation doses delivered to the patient (e.g., ROIs and OARs) as determined by the MRgRT system 100 (e.g., the dose reconstruction cluster 150). The actual dose of radiation that was delivered a patient can be determined using MRI images (e.g., 4D MRI images) captured by the MRgRT system 100 (e.g., the MRI system 128) prior to, during, and/or post the administration of radiation therapy.

The MRgRT system 100 generates one or more radiation delivery configuration (608). Consistent with implementations of the current subject matter, the delivery configuration can include, for example, but not limited to, isocenter placement, and beam and/or IMRT or CRT configuration.

The MRgRT system 100 can provide a GUI via the user interface 130 to allow a user (e.g., radiotherapist) to manually place one or more isocenters indicating points on an ROI where radiation beams should pass through.

In some implementations of the current subject matter, the MRgRT system 100 can provide default beam configurations or templates for use with IMRT and/or CRT to assist a user in beam configuration. For example, default beam configurations or templates can be provided for one or more common ROIs including, for example, but not limited to, breast with tangents, breast with tangents and nodal irradiation, head and neck with low neck field, head and neck with separate low neck field, central nervous system, craniospinal, lung, prostate, whole pelvis, right and left hemi pelvis, whole pelvis with or without para-aortics, whole brain, vertebral body, mantle fields, and whole body fields.

Alternately or in addition, a user can create and save custom beam configurations as new templates. For example, the user can manually place one or more radiation beams using a beam-eye-view display provided by the MRgRT system 100. The user can place the radiation beams in a plurality of placement modes including, for example, but not limited to, 3-beam placement and single beam placement. In some implementations of the current subject matter, the MRgRT system 100 can provide beam transit time corresponding to the placement of individual radiation beams.

In some implementations of the current subject matter, one or more of placed radiation beams can be selected for IMRT. When a radiation beam is selected for IMRT, the MRgRT system 100 can provide a GUI for a user to indicate IMRT configuration parameters including, for example, but not limited to, prescription doses for ROIs, tolerance doses for OARs, and the relative importance of the ROIs and the OARs. In some implementations of the current subject matter, the MRgRT system 100 can provide IMRT templates that include optimized models for administering IMRT. The templates include predefined values that have been demonstrated to produce ideal results in previous cases. Alternately, a user can also create and save custom IMRT configurations as IMRT templates.

Consistent with implementations of the current subject matter, the MRgRT system 100 can optimize an IMRT configuration by performing one or more operations including, for example, but not limited to, fluence map optimization (e.g., performed using beamlet dose calculation), leaf sequencing, and segment ordering optimization. The MRgRT system 100 can further optimize the IMRT configuration by performing Monte Carlo simulations.

In some implementations of the current subject matter, the MRgRT system 100 performs a "warm start" optimization based on an original IMRT configuration and an original set of IMRT configuration parameters. Advantageously, a "warm start" optimization ensures that the optimized IMRT configuration is similar to the original IMRT configuration devised for a patient. However, adjusting one or more IMRT configuration parameters can steer the optimized IMRT configuration towards a more desirable, albeit divergent, solution.

The MRgRT system 100 generates one or more dose predictions based at least in part on the prescription and delivery configuration (610). Consistent with implementations of the current subject matter, the MRgRT system 100 can generate a dose prediction by applying the prescription and the delivery configuration to MRI images captured by the MRgRT system 100 (e.g., the MRI system 128) in order to detect any interplay and/or aliasing effects on dose delivery.

The MRgRT system 100 determines whether the dose predication meets one or more clinical objectives (611). If the MRgRT system 100 determines that the dose prediction meets the one or more clinical objectives (611-Y), the MRgRT system 100 generates a treatment plan that includes the prescription and the delivery configuration (612). Clinical objectives can include, for example, but not limited to, dose-volume constraints on a patient's anatomical structures (e.g., ROIs and OARs), minimum allowed doses for the patient's anatomical structures, maximum doses for the patient's anatomical structures, biologically effective doses or dose volume constraints, tumor control probabilities, and normal tissue (e.g., OAR) complication probabilities.

Alternately, if the MRgRT system 100 determines that the dose prediction does not meet the one or more clinical objectives (611-N), the MRgRT system 100 modifies at least one of the prescription and the delivery configuration (614). The MRgRT system 100 generates a dose prediction based on the prescription and the delivery configuration (610) and determines whether the dose prediction meets one or more clinical objectives (611).

In some implementations of the current subject matter, the MRgRT system 100 can be configured to perform the process 600 a priori (i.e., prior to patient arrival). Alternately or in addition, the MRgRT system 100 can be configured to perform the process 600 "on-table" (e.g., while a patient is present on the patient couch 124). Advantageously, the MRgRT system 100 is capable of performing the process 600 to generate a treatment plan in an efficient and timely manner (e.g., less than 2 minutes) for on-table treatment planning.

One or more operations of the process 600 can be performed in a different order than shown without departing from the scope of the present disclosure. Moreover, one or more operations of the process 600 can be repeated and/or omitted without departing from the scope of the present disclosure.

Figure 7:
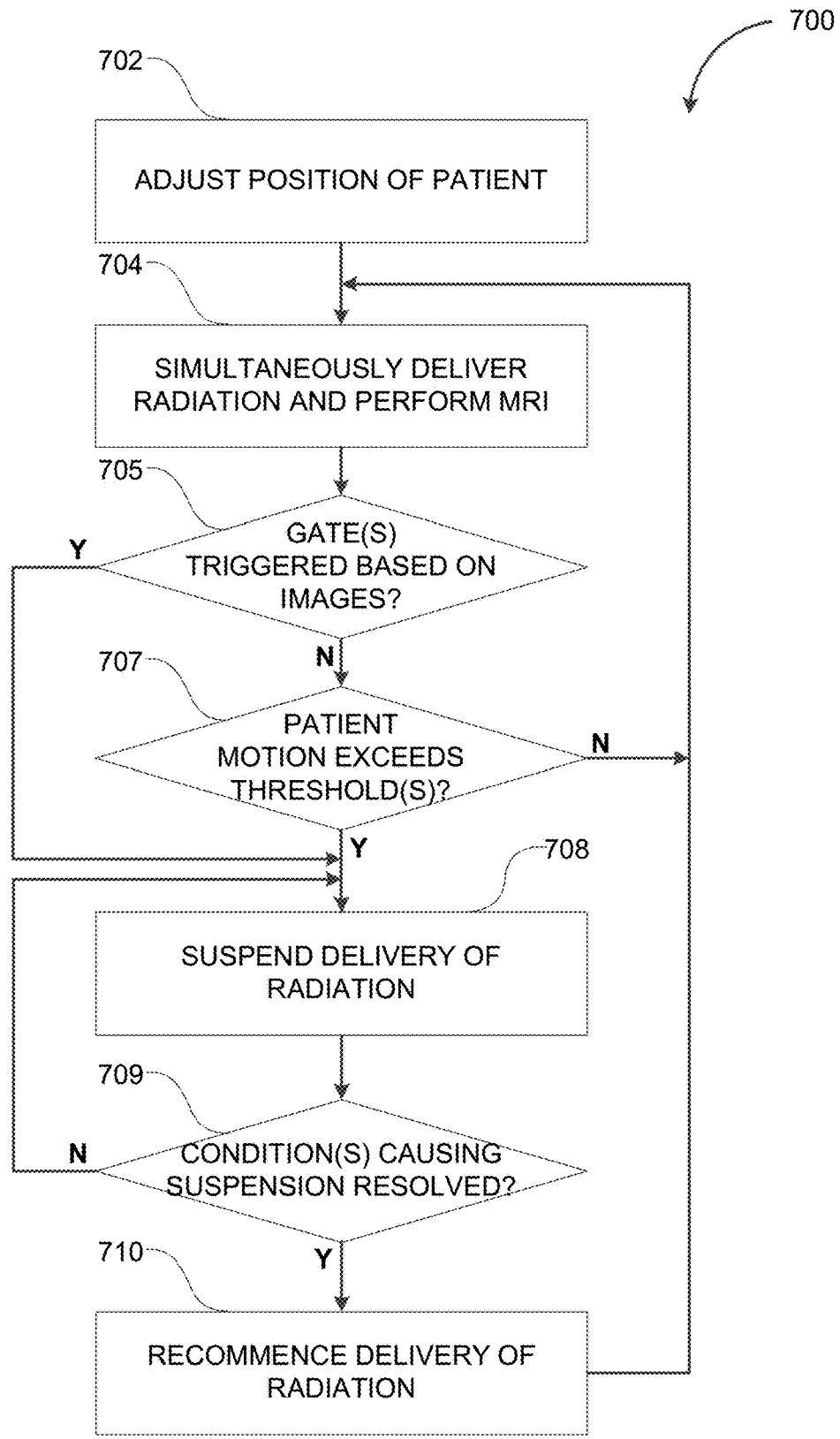
FIG. 7 is a flowchart illustrating a process for administering radiation therapy consistent with implementations of the current subject matter.

FIG. 7 is a flowchart illustrating a process 700 for administering radiation therapy consistent with implementations of the current subject matter. Referring to FIGS. 1, 5, and 7, the process 700 can be performed by the MRgRT system 100 and can implement operation 510 of the process 500 described with respect to FIG. 5.

The MRgRT system 100 adjusts the position of a patient (702). For example, the MRgRT system 100 can adjust the position of the patient including by adjusting the position of the patient couch 124. In some implementations of the current subject matter, the MRgRT system 100 can adjust patient position using a laser system to identify 3 orthogonal "landing points" marked on the skin of the patient. The MRgRT system 100 can store adjustments made during earlier radiation therapy sessions and automatically apply the same adjustments during subsequent radiation therapy sessions.

Additionally, the MRgRT system 100 can assist a user (e.g., a radiotherapist) in performing manual patient adjustments. For instance, the MRgRT system 100 can provide alerts if the lateral and/or vertical limits of couch motion are exceeded or if the patient (or the patient couch 124) is too close to the gantry 120 and/or the radiation therapy head 122. The MRgRT system 100 can also display (e.g., via the display 132 coupled to the user interface 130) the location of the isocenter as well as project the radiation beams placed according to the treatment plan. Additionally, the MRgRT system 100 can verify that the patient is properly positioned by obtaining one or more of orthogonal pilot scans and current primary planning volumes.

The MRgRT system 100 simultaneously delivers radiation and performs MRI (704). Consistent with implementations of the current subject matter, the MRgRT system 100 delivers radiation (e.g., via the radiation therapy heads 122) to a patient (e.g., on the patient couch 124) while also capturing MRI images (e.g., using the MRI system 128).

In some implementations of the current subject matter, the MRgRT system 100 can selectively save MRI images captured during radiation delivery. For example, the MRgRT system 100 can remove MRI images captured when radiation delivery is suspended (e.g., by the gating and/or interlock mechanism) and/or consolidate MRI images that do not depict patient motion in excess of a threshold (e.g., 2 mm).

The MRgRT system 100 determines whether one or more gates are triggered based on at least a portion of the MRI images captured during the delivery of radiation (705). Consistent with implementations of the current subject matter, a gating mechanism can be deployed during radiation delivery. The gating mechanism monitors the positions of one or more anatomical structures (e.g., ROIs and/or OARs) during radiation delivery relative to one or more spatial gates. The position of an anatomical structure can trigger a spatial gate if that anatomical structure shifts outside of the spatial gate (e.g., 3 mm). Additionally, a temporal gate can be triggered if the anatomical structure remains outside of the spatial gate for a length of time in excess of the temporal gate (e.g., 3 seconds).

The MRgRT system 100 may determine that one or more gates are not triggered based on at least a portion of the MRI images captured during the delivery of radiation (705-N). For example, the position of the anatomical structure may remain within the one or more spatial gates. Alternately, the position of the anatomical structure may shift outside of the one or more spatial gate but not for a period of time that exceeds a temporal gate. As such, the MRgRT system 100 determines whether patient motion exceeds one or more interlock thresholds based on at least a portion of the MRI images captured during the delivery of radiation (707). In some implementations of the current subject matter, an interlock mechanism can be deployed during radiation delivery. The interlock mechanism detects patient motion based on planar MRI images and suspends radiation delivery in response to detecting patient motion that exceeds one or more thresholds.

If the MRgRT system 100 determines that patient motion exceeds one or more interlock thresholds (707-Y), the MRgRT system 100 suspends the delivery of radiation (708). Alternately, if the MRgRT system 100 determines that patient motion does not exceed one or more interlock thresholds (707-N), the MRgRT system 100 continues to simultaneously deliver radiation and perform medical imaging (704).

Alternately, if the MRgRT system 100 determines that one or more gates are triggered based at least a portion of the MRI images captured during the delivery of radiation (705-Y), the MRgRT system 100 suspends the delivery of radiation (708). For example, the position of the anatomical structure may shift outside of the one or more spatial gates. Additionally, the position of the anatomical structure may shift outside of the one or more spatial gates for a period of time exceeding a temporal gate. Accordingly, the MRgRT system 100 can determine that one or more gates are triggered and suspend radiation delivery.

The MRgRT system 100 determines whether one or more conditions causing the suspension of radiation delivery are resolved (709). For example, the MRgRT system 100 can determine whether the anatomical structure has returned to a position inside of the spatial gate. The MRgRT system 100 can also determine whether patient motion in excess of the one or more thresholds has ceased.

If the MRgRT system 100 determines that the one or more conditions causing the suspension of radiation delivery are resolved (709-Y), the MRgRT system 100 recommences delivery of radiation (710). The MRgRT system 100 continues to simultaneously deliver radiation and perform medical imaging (704). Alternately, if the MRgRT system 100 determines that the one or more conditions triggering the one or more gates are not resolved (709-N), the MRgRT system 100 will continue to suspend the delivery of radiation (706).

One or more operations of the process 700 can be performed in a different order than shown without departing from the scope of the present disclosure. Moreover, one or more operations of the process 700 can be repeated and/or omitted without departing from the scope of the present disclosure.

Figure 8:
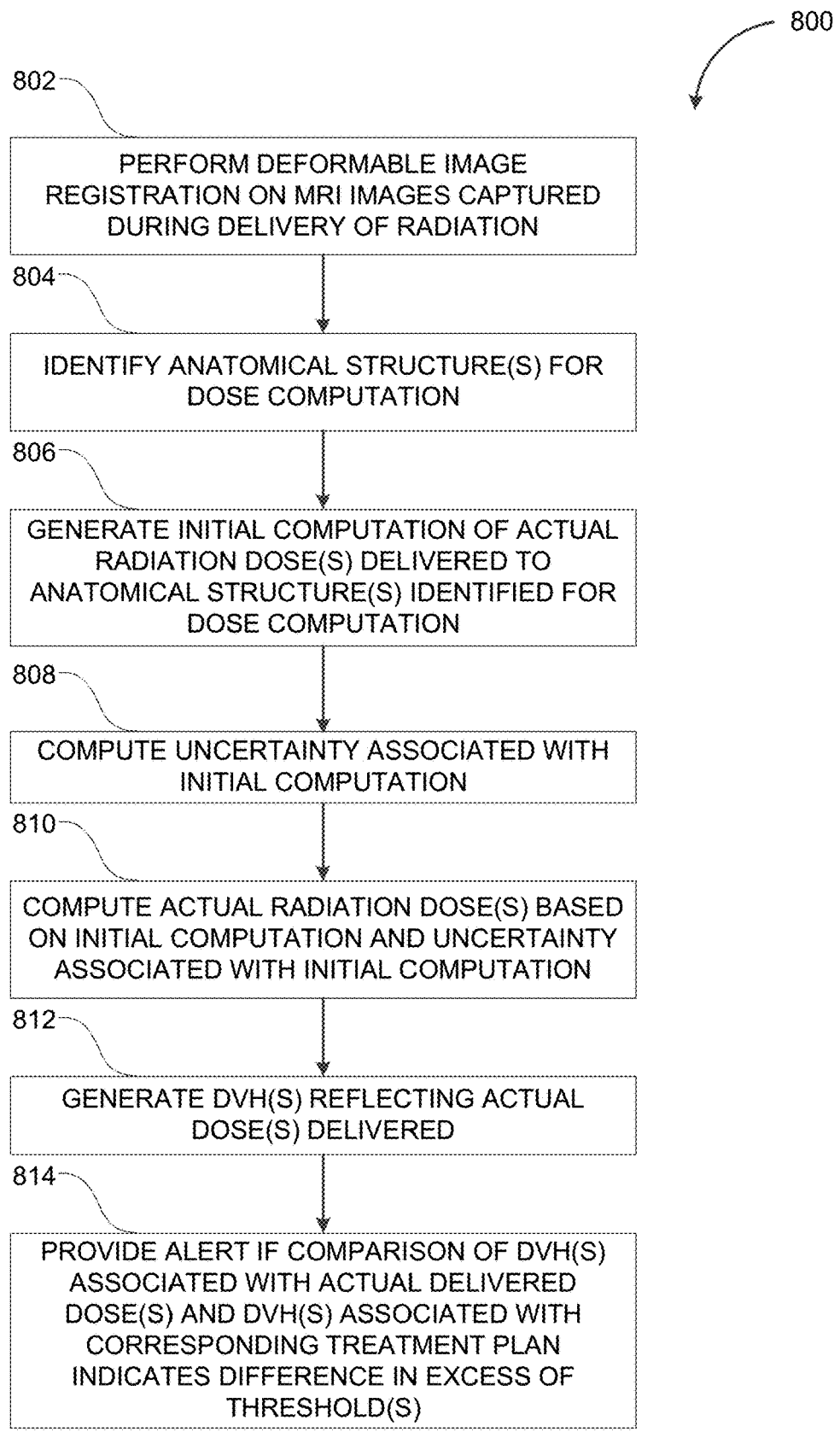
FIG. 8 is a flowchart illustrating a process for dose computation consistent with implementations of the current subject matter.

FIG. 8 is a flowchart illustrating a process 800 for dose computation consistent with implementations of the current subject matter. Referring to FIGS. 1, 7, and 8, the process 800 can be performed by the MRgRT system 100 (e.g., the dose reconstruction cluster 180) and can implement operation 512 of the process 500 described with respect to FIG. 5.

The MRgRT system 100 performs deformable image registration on MRI images captured during the delivery of radiation (802). For example, the MRgRT system 100 can perform deformable image registration on a series of MRI images captured by the MRI system 128 prior to, during, or post the administration of radiation therapy. In some implementations of the current subject matter, the MRgRT system 100 can track the absolute deviation of one or more anatomical structures (e.g., ROIs and OARs) from initial locations throughout the delivery of radiation.

The MRgRT system 100 identifies one or more anatomical structures for dose computation (804). The actual dose of radiation delivered is affected by patient motion (e.g., shift in patient organ geometry) during the delivery of radiation. Thus, in some implementations of the current subject matter, the MRgRT system 100 can flag anatomical structures that have moved in excess of a threshold for dose computation whereas anatomical structures that did not demonstrate motion exceeding the threshold are bypassed for dose computation. Alternately or in addition, the MRgRT system 100 can correlate the MRI images captured by the MRgRT system 100 (e.g., the MRI system 128) with radiation beam shapes and fluences through the patient to determine one or more anatomical structures that were not exposed to radiation. The MRgRT system 100 can flag anatomical structures that were exposed to radiation for dose computation while anatomical structures that were not exposed to radiation can be bypassed for dose computation.

The MRgRT system 100 generates an initial computation of the actual radiation doses delivered to the one or more anatomical structures identified for dose computation (806). Consistent with implementations of the current subject matter, the MRgRT system 100 can perform a scaled density finite sized pencil beam algorithm to generate the initial computation of the actual radiation doses delivered. Alternately or in addition, the MRgRT system 100 can perform a time dependent Monte Carlo simulation that incorporates control data and MRI images captured by the MRgRT system 100 (e.g., the MRI system 128) during radiation delivery.

In addition to patient motion, the actual dose of radiation delivered to the patient can also be affected by interruptions to the delivery of radiation caused by the gating mechanism and/or the interlock mechanism. For example, the gating mechanism and/or the interlock mechanism can cause a series of suspensions in radiation delivery thereby changing the actual dose of radiation delivered to the patient including, for example, but not limited to, shutter dose effects and truncation errors for radiation doses below a safely deliverable threshold. Accordingly, the MRgRT system 100 is configured to generate an initial computation that accounts for the effects of the interruptions to radiation delivery caused by the gating mechanism and/or the interlock mechanism. For example, the MRgRT system 100 can record and account dose variations during radiation delivery and account for such variations when computing the actual dose of radiation delivered to the patient.

The MRgRT system 100 computes an uncertainty associated with the initial computation (808). The MRgRT system 100 computes one or more actual radiation doses based at least in part on the initial computation and the uncertainty associated with the initial computation (810). Uncertainty associated with the initial computation of radiation doses can arise due to the random nature of Monte Carlo simulations. Additionally, uncertainty associated with the initial computation can arise during the course of deformable image registration. For example, deformable image registration provides a probabilistic outcome based on the absolute magnitude of the deformation and the change in connectivity in neighboring voxels. As such, the MRgRT system 100 can compute the actual radiation dose by interpolating a distribution of the initial computation and the uncertainty associated with the initial computation.

The MRgRT system 100 generates one or more DVHs reflecting the actual doses delivered (812). The MRgRT system 100 compares the DVHs associated with the actual delivered dose with DVHs associated with a corresponding treatment plan (814). The MRgRT system 100 provides an alert if the comparison between the DVHs associated with the actual delivered doses and the DVHs associated with a corresponding treatment plan indicates a difference in excess of one or more thresholds (814). For example, the MRgRT system 100 can issue a warning (e.g., to a clinician) in the event that a discrepancy between the actual radiation dose delivered to a patient and the radiation dose prescribed in a treatment plan exceeds one or more thresholds including, for example, but not limited to, coverage volume, and hot and cold spots in dose distribution.

One or more operations of the process 800 can be performed in a different order than shown without departing from the scope of the present disclosure. Moreover, one or more operations of the process 800 can be repeated and/or omitted without departing from the scope of the present disclosure.

Figure 9:
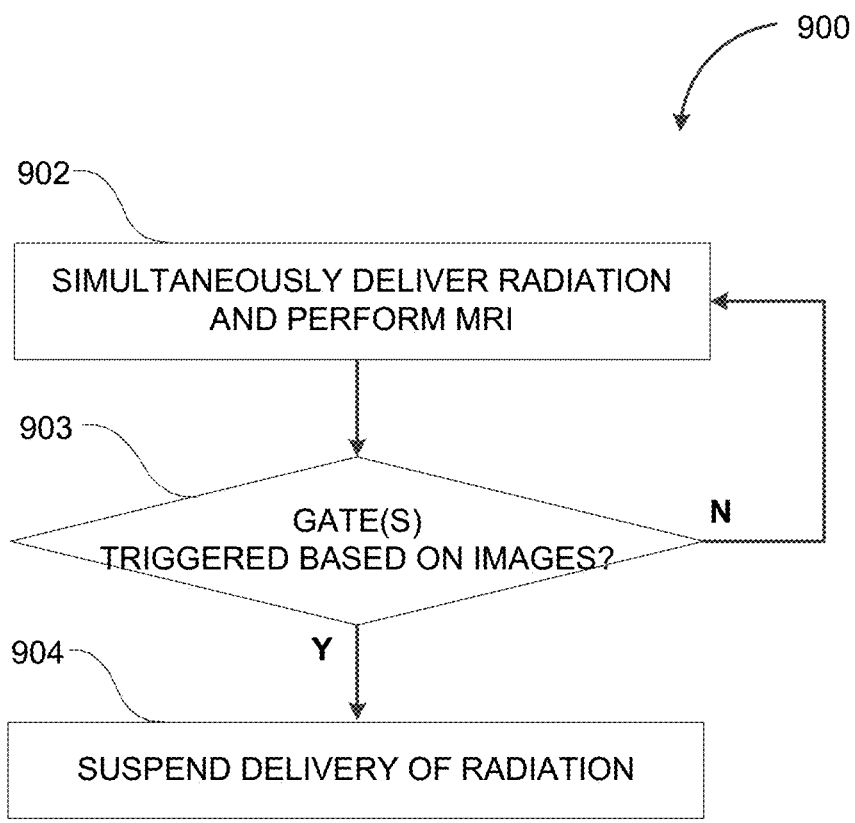
FIG. 9 is a flowchart illustrating a process for administering radiation therapy consistent with implementations of the current subject matter.

FIG. 9 is a flowchart illustrating a process 900 for administering radiation therapy consistent with implementations of the current subject matter. Referring to FIGS. 1, 5, and 9, the process 900 can be performed by the MRgRT system 100 and can implement operation 510 of the process 500 described with respect to FIG. 5.

The MRgRT system 100 simultaneously delivers radiation and performs MRI (902). The MRgRT system 100 determines whether one or more gates are triggered based on at least a portion of the MRI images captured during the delivery of radiation (903). For example, the MRgRT system 100 can use the MRI images captured during the delivery of radiation to determine whether one or more spatial and/or temporal gates are triggered.

The MRgRT system 100 can determine that one or more gates are not triggered based on at least a portion of the MRI images captured during the delivery of radiation (903-N). For example, the position of the anatomical structure may remain within the one or more spatial gates. Alternately, the position of the anatomical structure may shift outside of the one or more spatial gate but not for a period of time that exceeds a temporal gate. As such, the MRgRT system continues to deliver radiation and perform MRI (902).

Alternately, if the MRgRT system determines that one or more gates are triggered based on at least a portion of the MRI images captured during the delivery of radiation (903-Y), the MRgRT system 100 suspends the delivery of radiation (904).

One or more operations of the process 900 can be performed in a different order than shown without departing from the scope of the present disclosure. Moreover, one or more operations of the process 900 can be repeated and/or omitted without departing from the scope of the present disclosure.

Implementations of the present disclosure can include, but are not limited to, methods consistent with the descriptions provided above as well as articles that comprise a tangibly embodied machine-readable medium operable to cause one or more machines (e.g., computers, etc.) to result in operations implementing one or more of the described features. Similarly, computer systems are also described that can include one or more processors and one or more memories coupled to the one or more processors. A memory, which can include a computer-readable storage medium, can include, encode, store, or the like one or more programs that cause one or more processors to perform one or more of the operations described herein. Computer implemented methods consistent with one or more implementations of the current subject matter can be implemented by one or more data processors residing in a single computing system or multiple computing systems. Such multiple computing systems can be connected and can exchange data and/or commands or other instructions or the like via one or more connections, including but not limited to a connection over a network (e.g. the Internet, a wireless wide area network, a local area network, a wide area network, a wired network, or the like), via a direct connection between one or more of the multiple computing systems, etc.

One or more aspects or features of the subject matter described herein can be realized in digital electronic circuitry, integrated circuitry, specially designed application specific integrated circuits (ASICs), field programmable gate arrays (FPGAs) computer hardware, firmware, software, and/or combinations thereof. These various aspects or features can include implementation in one or more computer programs that are executable and/or interpretable on a programmable system including at least one programmable processor, which can be special or general purpose, coupled to receive data and instructions from, and to transmit data and instructions to, a storage system, at least one input device, and at least one output device. The programmable system or computing system can include clients and servers. A client and server are generally remote from each other and typically interact through a communication network. The relationship of client and server arises by virtue of computer programs running on the respective computers and having a client-server relationship to each other.

These computer programs, which can also be referred to programs, software, software applications, applications, components, or code, include machine instructions for a programmable processor, and can be implemented in a high-level procedural language, an object-oriented programming language, a functional programming language, a logical programming language, and/or in assembly/machine language. As used herein, the term "machine-readable medium" refers to any computer program product, apparatus and/or device, such as for example magnetic discs, optical disks, memory, and Programmable Logic Devices (PLDs), used to provide machine instructions and/or data to a programmable processor, including a machine-readable medium that receives machine instructions as a machine-readable signal. The term "machine-readable signal" refers to any signal used to provide machine instructions and/or data to a programmable processor. The machine-readable medium can store such machine instructions non-transitorily, such as for example as would a non-transient solid-state memory or a magnetic hard drive or any equivalent storage medium. The machine-readable medium can alternatively or additionally store such machine instructions in a transient manner, such as for example as would a processor cache or other random access memory associated with one or more physical processor cores.

To provide for interaction with a user, one or more aspects or features of the subject matter described herein can be implemented on a computer having a display device, such as for example a cathode ray tube (CRT) or a liquid crystal display (LCD) or a light emitting diode (LED) monitor for displaying information to the user and a keyboard and a pointing device, such as for example a mouse or a trackball, by which the user may provide input to the computer. Other kinds of devices can be used to provide for interaction with a user as well. For example, feedback provided to the user can be any form of sensory feedback, such as for example visual feedback, auditory feedback, or tactile feedback; and input from the user can be received in any form, including, but not limited to, acoustic, speech, or tactile input. Other possible input devices include, but are not limited to, touch screens or other touch-sensitive devices such as single or multi-point resistive or capacitive trackpads, voice recognition hardware and software, optical scanners, optical pointers, digital MRI image capture devices and associated interpretation software, and the like.

In the descriptions above and in the claims, phrases such as "at least one of" or "one or more of" may occur followed by a conjunctive list of elements or features. The term "and/or" may also occur in a list of two or more elements or features. Unless otherwise implicitly or explicitly contradicted by the context in which it used, such a phrase is intended to mean any of the listed elements or features individually or any of the recited elements or features in combination with any of the other recited elements or features. For example, the phrases "at least one of A and B;" "one or more of A and B;" and "A and/or B" are each intended to mean "A alone, B alone, or A and B together." A similar interpretation is also intended for lists including three or more items. For example, the phrases "at least one of A, B, and C;" "one or more of A, B, and C;" and "A, B, and/or C" are each intended to mean "A alone, B alone, C alone, A and B together, A and C together, B and C together, or A and B and C together." Use of the term "based on," above and in the claims is intended to mean, "based at least in part on," such that an unrecited feature or element is also permissible.

The subject matter described herein can be embodied in systems, apparatus, methods, and/or articles depending on the desired configuration. The implementations set forth in the foregoing description do not represent all implementations consistent with the subject matter described herein. Instead, they are merely some examples consistent with aspects related to the described subject matter. Although a few variations have been described in detail above, other modifications or additions are possible. In particular, further features and/or variations can be provided in addition to those set forth herein. For example, the implementations described above can be directed to various combinations and subcombinations of the disclosed features and/or combinations and subcombinations of several further features disclosed above. In addition, the logic flows depicted in the accompanying figures and/or described herein do not necessarily require the particular order shown, or sequential order, to achieve desirable results. Other implementations can be within the scope of the following claim.

What is claimed is:

1. A system comprising:
a radiation therapy system; and
a non-transitory machine-readable medium storing instructions which, when executed by at least one programmable processor, cause the at least one programmable processor to perform operations comprising:
recording patient registration information, wherein the patient registration information comprises biometric information;
receiving patient identification information prior to a radiation therapy treatment by the radiation therapy system;
requiring authentication based on the patient registration information and the patient identification information prior to the radiation therapy system delivering radiation therapy treatment; and
delivering the radiation therapy treatment.

2. The system of claim 1, wherein the system further comprises a magnetic resonance imaging system.

3. The system of claim 1, wherein the patient identification information received prior to radiation therapy treatment comprises biometric information.

4. The system of claim 1, wherein the authentication is based on more than one type of patient registration information and patient identification information.

5. A system comprising:
a radiation therapy system; and
a non-transitory machine-readable medium storing instructions which, when executed by at least one programmable processor, cause the at least one programmable processor to perform operations comprising:
recording patient registration information, wherein the patient registration information comprises a photograph;
receiving patient identification information prior to a radiation therapy treatment by the radiation therapy system;
requiring authentication based on the patient registration information and the patient identification information prior to the radiation therapy system delivering radiation therapy treatment; and
delivering the radiation therapy treatment.

6. The system of claim 5, wherein the system further comprises a magnetic resonance imaging system.

7. The system of claim 5, wherein the patient identification information received prior to radiation therapy treatment comprises a photograph.

8. The system of claim 5, wherein the authentication is based on more than one type of patient registration information and patient identification information.

9. A system comprising:
a radiation therapy system; and
a non-transitory machine-readable medium storing instructions which, when executed by at least one programmable processor, cause the at least one programmable processor to perform operations comprising:
recording patient registration information;
receiving patient identification information prior to a radiation therapy treatment by the radiation therapy system, wherein the patient identification information received prior to radiation therapy treatment comprises a social security number;
requiring authentication based on the patient registration information and the patient identification information prior to the radiation therapy system delivering radiation therapy treatment; and
delivering the radiation therapy treatment.

10. The system of claim 9, wherein the system further comprises a magnetic resonance imaging system.

11. The system of claim 9, wherein the patient registration information comprises a social security number.

12. The system of claim 9, wherein the authentication is based on more than one type of patient registration information and patient identification information.

* * * * *